United States Patent [19]

Lee et al.

[11] Patent Number: 5,147,529
[45] Date of Patent: Sep. 15, 1992

[54] METHOD FOR AUTOMATICALLY PROCESSING MAGNETIC SOLID PHASE REAGENTS

[75] Inventors: Ching-Cherng Lee, Newark; James E. Davis, Wilmington, both of Del.

[73] Assignee: E. I. Du Pont de Nemours and Company, Wilmington, Del.

[21] Appl. No.: 230,449

[22] Filed: Aug. 10, 1988

[51] Int. Cl.$^5$ ............................................. G01N 35/04
[52] U.S. Cl. ........................................ 210/695; 436/45; 436/47; 436/177; 436/526
[58] Field of Search .......................... 209/223.2, 212.2; 436/526, 45, 47, 177; 210/695

[56] References Cited

U.S. PATENT DOCUMENTS

| | | | |
|---|---|---|---|
| 3,953,997 | 5/1976 | Wale | 72/128 |
| 4,066,537 | 1/1978 | Bernfeld | 209/223 R |
| 4,628,037 | 12/1986 | Chagnon et al. | 436/526 |
| 4,661,408 | 4/1987 | Lau et al. | 428/405 |
| 4,698,302 | 10/1987 | Whitehead et al. | 435/94 |
| 4,908,186 | 3/1990 | Sakamaki | 422/64 |

OTHER PUBLICATIONS

"Magnetic Affinity Chromatography Starter Kit M4001 and Magnetic Affinity Chromatography Support Biomag M4001" information sheet, Advanced Magnetics Inc. Jul. 1984.

*Primary Examiner*—Richard L. Raymond
*Assistant Examiner*—Brian Burn

[57] ABSTRACT

Magnetic particles used as a solid support are placed in reaction vessels and stepped sequentially past successive magnets for separation.

9 Claims, 4 Drawing Sheets

METHOD FOR AUTOMATICALLY PROCESSING MAGNETIC SOLID PHASE REAGENTS

FIELD OF THE INVENTION

The present invention relates to an automated method of and apparatus for the separation and concentration of analyte in small amounts of complex liquid mixtures.

BACKGROUND OF THE INVENTION

Separation, isolation and concentration are process steps common to a chemical analysis. Often these steps are taken to remove interfering substances so that a subsequent chemical analysis can be performed. This "separation" stage can be performed several ways including solvent extraction, solvent evaporation and resin exchange. Magnetic separation, another technique for removing interfering substances, is a process of separation, isolation and concentration where the sought-for substance is attached or bound to magnetic particles. The magnetic particles offer advantages of handling including speed, convenience and low energy input. It is particularly suited to handling small samples. Advanced Magnetics Inc. of Cambridge, Mass. has been very active in this field in the application of their super paramagnetic particles to separation techniques. Their usage and properties is described in a product bulletin entitled Magnetic Affinity Chromatography Starter Kit M4001 and Magnetic Affinity Chromatography Support Biomag TM M4100 dated July 1984.

Magnetic particles are particularly useful in heterogeneous immunoassays as a solid support. To be useful as a solid support, the particles must be derivatized to permit the attachment of bioactive protein. Hersh et al. in their U.S. Pat. No. 3,953,997 describe the use of magnetically responsive particles for this purpose and use functionalized silanes as the intermediate between the particles and the bioactive protein.

There are essentially two types of heterogeneous immunoassays. These are competitive immunoassays and sandwich immunoassays. In a competitive assay, an antibody to an antigen contained in a first reagent is attached to the derivatized magnetic particles to make up a solid phase. The second reagent, consisting of antigen attached to a tag (a measurable entity, including radioactive molecules, fluorescent molecules, or enzymes), and patient sample are mixed with the solid phase in a test tube. In the absence of patient antigen, some 50% of the antigen-tag is bound to the antibody of the magnetic solid phase. In the presence of patient antigen, some of the antibodies are filled up with patient antigen and are unavailable to the tag antigen. As a result increasing amounts of patient antigen leads to decreasing amount of tag antigen. Thus one can form a calibration chart relating the amount of patient antigen to the amount of tag. The separation stage results from the need to measure the free tag or the bound tag, not the total tag added. The magnetic particle facilitates this separation by forming the particles with the bound tag into a pellet on the side of the tube. The free tag can then be removed as by aspiration. Following the separation and removal of free tag, another reagent is added so that the amount of bound tag can be measured. In a typical case, enzyme is used as the tag so that the reagent added is a "substrate" for the enzyme permitting the measurement of the amount of tag that was bound to antibody.

In a typical the sandwich immunoassay, an antibody to an antigen is attached to the magnetic particle. This is in high concentration relative to the amount of patient antigen in a sample. Patient antigen is captured by the antibody on the magnetic particles and then the particles (and captured patient antigen) separated from interfering substances in the sample. To this, a second reagent, containing a second antibody with an attached tag, is added. This second antibody attaches to the patient antigen, captured by the first antibody on the magnetic particle, and results in the formation of a sandwich so that the second antibody tag is held firmly by the antigen to the first antibody on the magnetic particle. At this point, a magnetic separation similar to that described, permits the determination of bound tag which is in proportion to the patient antigen, the excess tag of the second reagent having been removed by aspiration.

Magnetic particles are particularly useful as the solid support in heterogeneous immunoassays because they can readily separate the free from the bound tag. Such immunoassays using magnetic particles as a solid support are described for example in U.S. Pat. No. 4,661,408 (Lau et al.), U.S. Pat. No. 4,628,037 issued to Chagnon et al., U.S. Pat. No. 4,672,040 issued to Josephson, and U.S. Pat. No. 4,698,302 issued to Whitehead et al. The methods disclosed in all of these patents relate to manual processes which utilize manual magnetic separation units such as those that are available from Corning Medical, Corning Glass Works, Medifield, Mass. Such manual techniques are relatively slow, require relatively strong magnets which are expensive, require considerable manual dexterity, and require an excessive amount of time to effect the separation with the purity required, particularly for sandwich type heterogeneous immunoassays.

Technicon Corporation has offered an automated heterogeneous magnetic immunoassay system for some years. In this system the reagents are combined in a continuous flow process. Having reacted the reagents together, the process then brings the stream through a magnetic field where the magnetic particles are captured and, bound tage measured. The problem with this process is that of continuous flow systems in general. Carryover from one sample to the next tends to produce erroneous results, which error is reduced by reducing the number of samples analyzed per hour.

SUMMARY OF THE INVENTION

Many of these problems of prior art systems and methods using magnetic particles, i.e., particles that are responsive to a magnetic field, are reduced using the apparatus and method of this invention. These permit magnetic particles to be used as a separable solid support in various analytical techniques in an automated fashion. This is particularly true in heterogeneous immunoassays. According to this invention, an automatic apparatus for separating particles from aqueous dispersions of such particles disposed in a plurality of reaction vessels, the particles being responsive to a magnetic field, comprises: a transport means for stepwise indexing the vessels in sequence to a plurality of processing positions, and a first frame having a plurality of magnets each located adjacent a different one of a selected number of consecutive processing positions.

In a preferred embodiment of the invention, the transport means indexes the vessels stepwise to the processing positions. The reaction vessels each have a longitudinal axis that is generally vertically disposed while the vessels are being indexed, at least two consecutively positioned magnets being positioned at different heights relative to the longitudinal axis of the vessels. The consecutively positioned magnets have alternate south and north poles adjacent the processing sequentially located positions and the apparatus includes an element having a low magnetic reluctance positioned adjacent the poles of two consecutively positioned magnets, the elements being remote from the processing positions, thereby providing a magnetic flux return path for the consecutively positioned magnetics. The magnet adjacent the last processing position of the frame has a magnetic flux that is greater than the flux of the remaining magnets.

Using this apparatus, a chemical analyzer using plural processing positions where the magnetic separation is accomplished over several processing positions is able to operate without the time delays that accompany the usual magnetic separation step. By positioning magnets, adjacent successive ones of the separation processing positions, at different heights, the separated particles from an extended region of the fluid are caused to clump together in a tight region on the wall of the reaction vessel. This facilitates introducing a probe into the reaction vessels to aspirate the liquid leaving the magnetic particles and improves the separation efficiency.

The invention also provides an automatic method for separating particles from aqueous dispersions of such particles disposed in a plurality of reaction vessels, the particles being responsive to a magnetic field comprising the steps of:

transporting the vessels in steps to a plurality of processing positions, and subjecting the vessels at each of a selected number of the processing positions to a magnetic field.

Preferably, the vessels have a longitudinal axis which is vertically positioned and the method includes orienting the vessel's longitudinal axes vertically while subjected to the magnetic field, and applying the magnetic field at different heights, at at least two consecutive processing positions, relative to the longitudinal axis of the vessel.

BRIEF DESCRIPTION OF THE DRAWINGS

The invention will be better understood with reference to the several drawings in which like reference numerals are used to indicate like components, in which.

DETAILED DESCRIPTION OF THE PREFERRED EMBODIMENT

Figure 1:
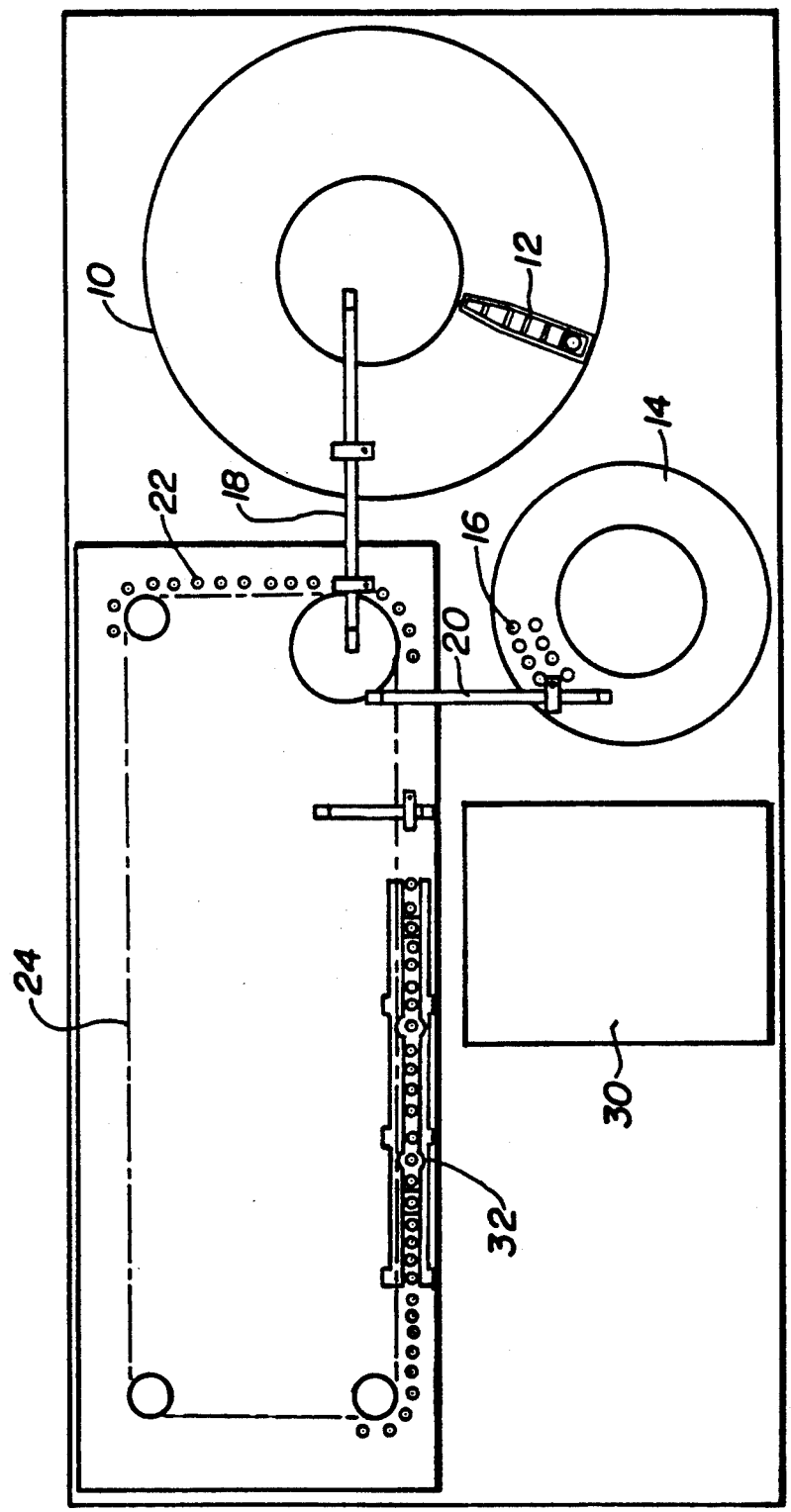
FIG. 1 is a schematic diagram of an automated chemical analyzer in which this invention finds particular use to provide the automated processing of magnetic solid phase reagents.

In FIG. 1 there may be seen, schematically presented, the elements of an automatic chemical analyzer, which may be conventional. This analyzer may include a reagent dispensing station 10 and may include reagent containers 12, which may be of any type, although the preferred container is a disposable plastic, multicompartmented container of the type used with the Dimension ™ Analyzer sold by E. I. du Pont de Nemours and Company, Wilmington, Del. Also, one of the compartments may be flexibly mounted at its top portion for vortexing to insure the magnetic particles, to be described, remain in suspension. The automatic apparatus also includes a sample carousel 14 adapted to hold sample containers 16 and suitable transfer arms 18 and 20, respectively, which may be of any conventional design. The transfer arm 18 contains a pipet device (not shown) for transferring liquid contained in the reagent containers 12 to reaction vessels 22 which are flexibly disposed on a transport 24.

The transport 24 may be chain driven, belt driven or, for that matter, a disc and move the reaction vessels stepwise to the several processing positions. Alternatively, the transport may move the vessels in a continuous manner to the several processing positions although this is not preferred. The stepwise or intermittent operation affords longer exposure of the vessels to the magnetic field and better separation. Whichever is used, the transport 24 provides a means for holding the reaction vessels 22 and for transporting the reaction vessels to several different processing positions. Similarly, a transfer arm 20 includes a pipet (not shown) for transferring the liquid contents of the samples to be analyzed 16 to the reaction vessels 22. Various wash buffers and other reagents may be stored in the area 30 to provide fluids and receptacles for the various aspiration and wash steps that are performed.

According to this invention, there is provided a wash station 32 which is uniquely configured to separate magnetic particles from (aqueous) dispersions of the particles in the several reaction vessels as they step through the automatic separating apparatus so provided. As the term is used herein, "magnetic particles" or simply "particles responsive to a magnetic field" may be any of those described above that are known in the art. They may be preferably ferromagnetic and having a small residual magnetism so that little clumping occurs in the absence of a magnetic field. Preferably particles of the type described by Lau et al. U.S. Pat. No. 4,661,408.

At the wash station 32, several functions are performed. These functions, as will be described in connection with FIG. 2, include adding reagent or wash to the reaction vessels prior to magnetic separation, mixing the contents of the vessels, magnetically separating the bound and free components in each vessel, aspirating the free fluid, adding new wash reagent, mixing and diluting and repeating these steps for several separate cycles.

Figure 2:
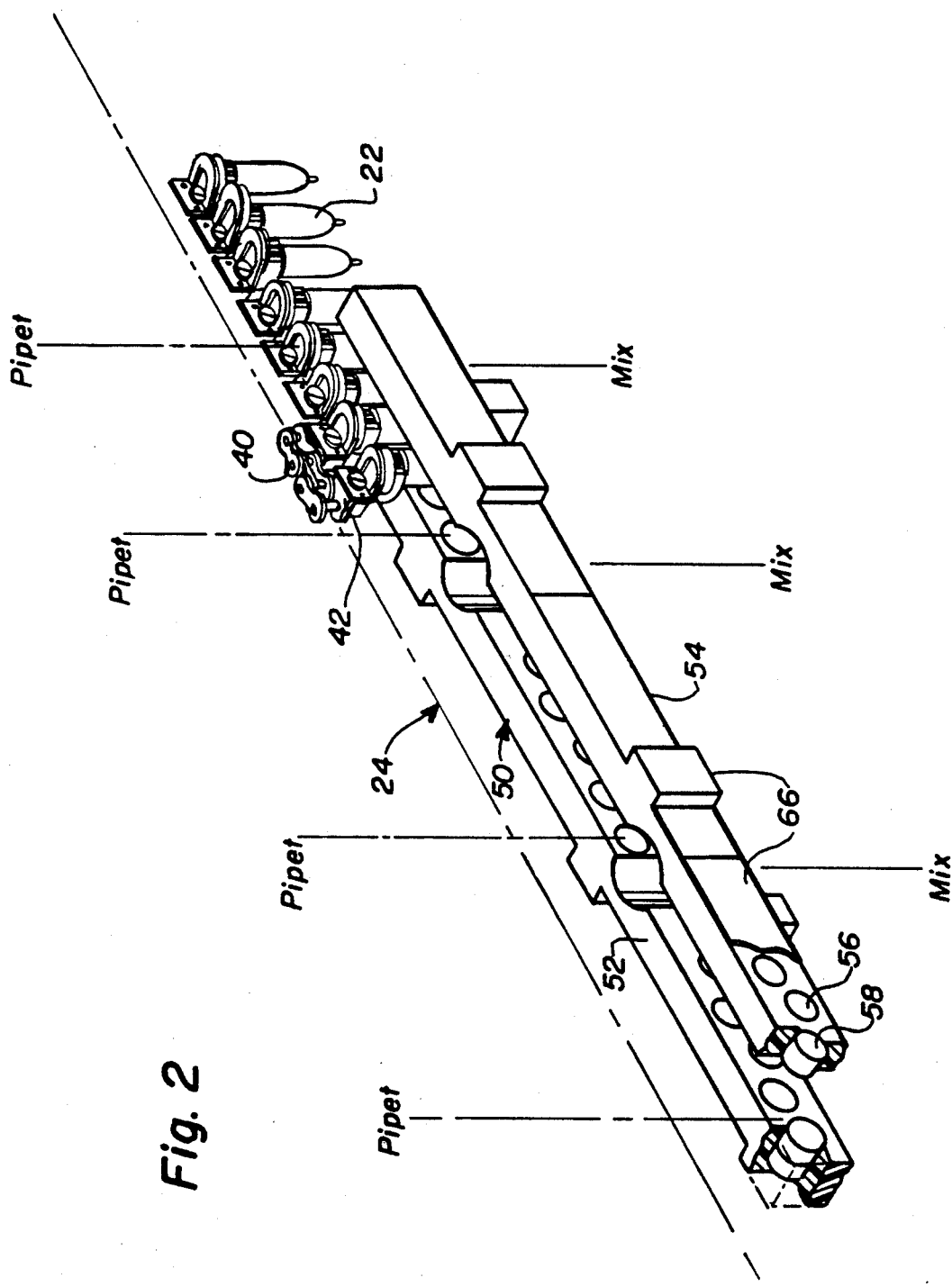
FIG. 2 is a pictorial representation of an assembly for positioning the magnets to receive the several reaction vessels being transported for magnetic separation.

As is seen more clearly in FIG. 2, the transport 24 is illustrated as having a chain 40 having brackets 42 which flexibly mount the reaction vessels 22 in a generally vertical position, the chain 40 moving in a generally horizontal plane. The reaction vessels 22, as may be seen, are longitudinal and have a vertically oriented longitudinal axis. While any flexible mounting means may be used for this purpose, a flexible mount utilizing a pair of flexible prongs which grasp the top of the reaction vessel 22 may be used. The interior surface of the prongs and the exterior surface of the vessel have longitudinal grooves and each respectively may mate to prevent rotation of the vessels about their axis during mixing. Thus held, the bottom of the vessels may be orbitted to vortex and mix the vessel's contents.

Figure 3:
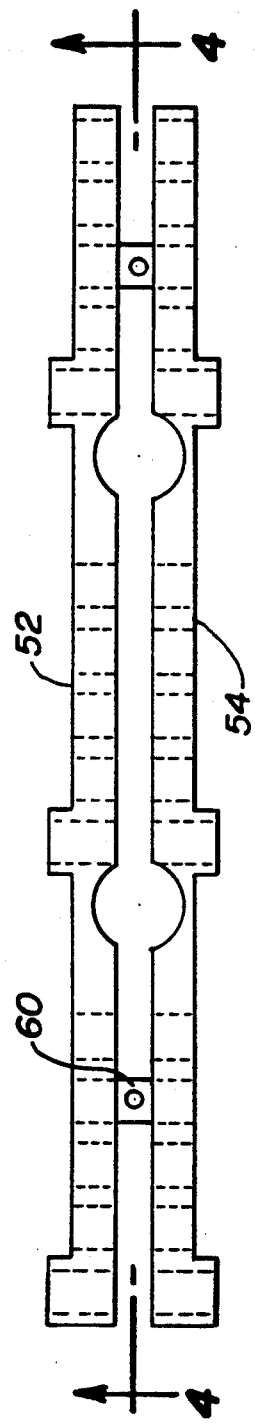
FIGS. 3, 4 and 5 are respectively plan, side elevation, and end elevation views of the magnetic separation assembly of this invention.

The vessels are aspirated by pipets at any of the several processing positions seen most clearly in FIG. 3. Similarly, mixing is provided at the first, sixth and thirteenth positions of a frame holding the separating magnets constructed in accordance with the preferred embodiment of this invention.

According to this invention, the frame may include first and second frame members 52 and 54, respectively, which are disposed in parallel relationship along the line of the transport 24. This permits the reaction vessels 22 to move (stepwise) between the frame members 52 and 54. The frame members 52 and 54 are constructed of any suitable nonmagnetic material, aluminum being preferred. Bores 56 are formed horizontally in the frame members at equally spaced intervals corresponding to the several step indexing processing positions of the transport 24 such that as the vessels 22 come to rest between their successive steps at the respective processing positions. The vessels at rest are directly opposite the open end of the respective bores 56. A magnet 58 is positioned in each bore with its end face directly adjacent or contiguous the vessels 22.

Figure 4:
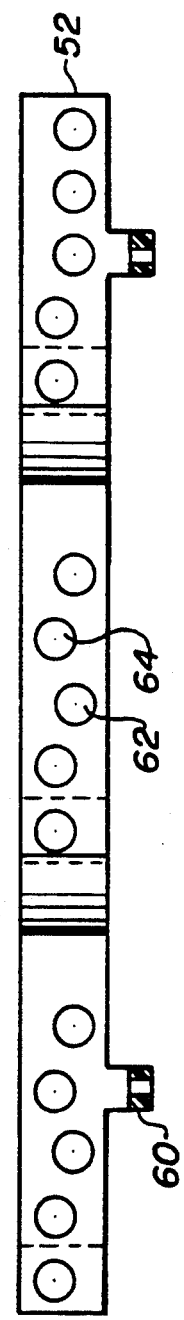
Figure 5:
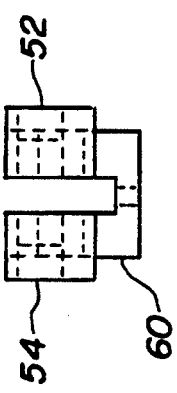
Figure 6A:
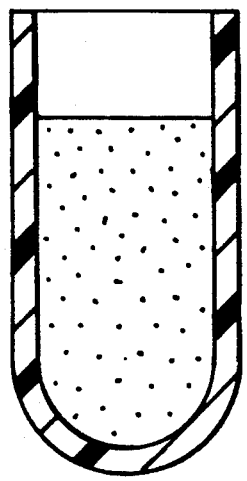
FIGS. 6 A, B, C and D are diagrammatic representations of various stages of the magnetic separation occurring in the magnetic assembly of FIGS. 2 through 5.
Figure 6B:
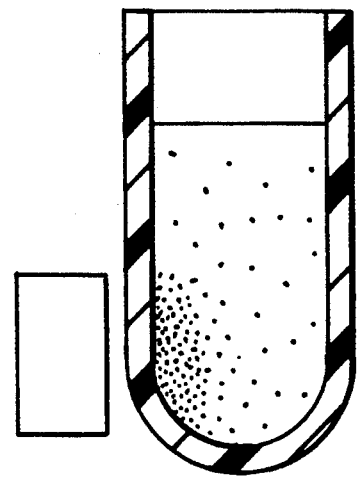
Figure 6C:
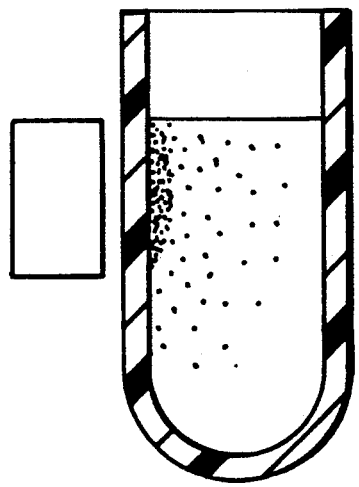
Figure 6D:
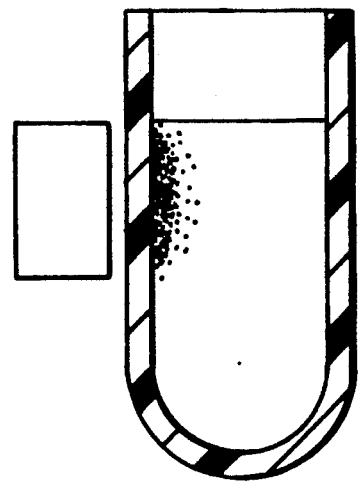

The structure of the frame 50 may be better understood in connection with FIGS. 3 through 5. As may be seen therein, the two frames are held together by crossmembers 60 secured to the bottom of the frames. Preferably these crossmembers 60 and the frame members 52, 54 are molded or cast as a single unit.

As may be seen most clearly in FIG. 3, the frame is constructed with three like section to permit three sequential, separate magnetic separations (cycles), as the reaction vessels are indexed between the frame members. The first separation or cycle is effected using the first five magnet positions, which comprise the first section, with the last or fifth position comprising preferably two magnets positioned in series to provide a greater magnetic flux. The next, or sixth position, the beginning of the middle section includes an enlarged region in the slot between the two frame members to facilitate orbital or vortex mixing of the vessel. The seventh position contains no magnet. The eighth, ninth, tenth, and eleventh positions each contain magnets and the twelfth position two serially positioned magnets, similar to the fifth position. The final section is duplicative of the middle section containing six reaction positions thirteen through nineteen.

As may be seen most clearly in FIG. 4 the magnets 58 may be placed at higher and lower vertical positions 62, 64, relative to the vertically disposed longitudinal axis of the reaction vessels. This difference in height relative to the longitudinal axis of the vessels facilitates separating all the magnetic particles first from the bottom portion of the vessels and then from the upper region of the vessels. When the reaction vessels first enter the wash 32 the first three magnets separate particles from the lower region of the vessels; thereafter, the next two positions separate particles from the upper region of the vessels. The middle and final section magnets are positioned vertically in alternating lower and higher positions relative to the vessels.

In a preferred embodiment of the invention, the polarity of the magnets are alternated such that first a north and then a south pole (or vice versa) is contiguous or adjacent the reaction vessels as they pass through the frame 50. When this configuration is used, a ferromagnetic plate 66 may be secured by suitable means to the outer sides of the frame interconnecting the magnet positions to provide a low reluctance return path for the exterior flux of the magnets.

Of course, only a single frame member need be used on one side of the reaction vessel path although the double frame is preferred because of the higher magnetic field strength available. When the two frame members 56, 54 are used, the opposed magnets in the respective frame members should have opposite poles facing each other. Alternating polarity magnets need not be used and all magnets may have the same pole facing adjacent the processing positions, but this is not preferred.

In operation, as the reaction vessels 22 are indexed toward the frame 50, at the processing position immediately preceding the frame, wash is added to the reaction vessel by a pipet and the vessel is vortexed to effect mixing of the now diluted particle reagent. Upon entering the frame 50, as stated above, the first three magnets preferably are positioned to apply the field to the lower portion of the reaction vessels so as to remove all magnetic particles in the aqueous dispersion contained in the vessels from the bottom of the vessels. Those in the bottom are the heavier particles. The next two magnets (i.e., those in the fourth and fifth positions, of the frame) are at a higher elevation relative to the vertical axis of the reaction vessels to remove or separate the magnetic particles from the upper portion of the reaction vessels. Also at this fifth position, two magnets are plated in series to provide a higher strength flux to insure that all magnetic particles are clustered on the side wall(s) of the reaction vessels and separated from the dispersion. At the same fifth position the vessels are aspirated following which a wash reagent is added. The first separation cycle is complete.

At the next or sixth position, wash reagent is added and mixing is effected. The next position seven is a rest position to permit the wash to continue. Thereafter the entire cycle of separation, aspiration and washing repeats itself two times before it leaves the frame 50. Substrate addition and incubation are effected before measurement occurs. In this connection, the reaction vessels themselves may be polypropylene which being translucent requires aspiration for measurement. Alternatively the reaction vessels may be an acrylic resin such as polymethylacrylate which is optically clear and may be positioned in a photometer itself for measurement.

The advantages of this step by step magnetic separation apparatus of this invention are many. To begin with, it facilitates the automatic separation of the magnetic particles from the aqueous dispersion of such particles which is necessary in heterogeneous immunoassays. Further the use of multiple magnets speeds up the instrument in which magnetic separation is necessary since the dwell at each processing position is relatively short. If dwell were to occur at one position for the time necessary to effect full separation, the entire analyzer apparatus would be slowed. Instead, multiple magnet positions are used with a short dwell at each position. Under these conditions, complete magnetic separation typically does not occur at a single processing position, but rather occurs as the reaction vessel is sequentially processed past the several magnets. The structure of the frame in this position permits its use with the conventional disc or chain transport instruments using only one direction of motion, i.e., that of the transport.

The use of the alternating north and south pole magnets contiguous the several processing positions with the use of a low reluctance strip behind the magnets, increases the field strength available and more importantly provides a greater magnetic field gradient which is preferred to effectively separate the particles from the liquid.

By vertically displacing the magnets along the longitudinal axis of the reaction vessels, magnets of a smaller cross-sectional area and size may be used thereby permitting the use of less costly magnet materials. It is preferred that the magnets provide 2000 gauss at the center of each reaction vessel. Any of the many commercially available magnets may be used; however, Neodymium-Iron magnets are preferred. The magnets which are positioned higher relative to the longitudinal axis of the reaction vessels are positioned so as to be somewhat in alignment with the upper portion of the liquid in the vessels, whereas the lower positioned magnets are more in the region of the lower portion of the cuvette. The magnets should not be speed greater along the longitudinal axis than the diameter of each magnet relative to each other.

This positioning of the magnets may be seen most clearly in FIG. 6. Starting with the uniform particle dispersion seen in FIG. 6A, as a reaction vessel moves horizontally into the frame 50, the initial lower magnets begins to collect particles from the lower portion of the reaction vessel as seen in FIG. 6B. The next position, shown in FIG. 6C, being higher along the longitudinal axis of a vessel, collects those particles in the higher region of the reaction vessel. Finally in FIG. 6D, the magnet positioned again in the upper portion, tends to collect virtually all the particles into a clump at the side so the separation is complete and a probe may enter the vessel to aspirate the liquid.

The reason the double frame is preferred is that, with the higher field strength permitted, and also because of the positioning of a magnet on either side of each processing position, the distance that the particles have to travel to be separated from the liquid, is only one half the diameter of the cuvette. The particles clump on each side of each vessel. It is thus seen that the automatic apparatus of this invention in which the reaction vessels are passed through plural magnet positions results in a higher throughput, lower cost, more effective analysis system.

What is claimed is:

1. An automatic method for separating particles from liquid dispersions of such particles disposed in a plurality of reaction vessels, the particles being responsive to a magnetic field comprising the steps of:
   transporting the vessels to a plurality of processing positions, and
   subjecting each of the vessels at at least two consecutive processing positions, to a magnetic field for a dwell time at each position less than that required to effect a complete separation of the particles from the dispersion.

2. The method of claim 1 wherein the vessels have a longitudinal axis and includes the steps of:
   orienting the vessels longitudinal axes vertically while subjected to the magnetic field, and
   applying the magnetic field to different heights, relative to the longitudinal axis of the vessel.

3. The method of claim 2 wherein the magnetic field is applied in opposite senses at the consecutive processing positions.

4. The method of claim 3 which includes the step of subjecting the vessels at the last of the selected processing positions to a stronger magnetic field than at the remaining positions.

5. The method of claim 1 wherein the magnetic field is applied in opposite senses at the selected consecutive processing positions.

6. The method of claim 1 wherein the transporting means transports the vessels in a stepwise manner to each processing position.

7. The method of claim 6 wherein the vessels have a longitudinal axis and includes the steps of:
   orienting the vessels longitudinal axes vertically while subjected to the magnetic field, and
   applying the magnetic field to different heights, at at least two consecutive processing positions, relative to the longitudinal axis of the vessel.

8. The method of claim 7 wherein the magnetic field is applied in opposite senses at the selected consecutive processing positions.

9. The method of claim 6 wherein the magnetic field is applied in opposite senses at the selected consecutive processing positions.

* * * * *